United States Patent
Smith et al.

(10) Patent No.: US 11,819,847 B2
(45) Date of Patent: Nov. 21, 2023

(54) NANOFLUIDIC DEVICE WITH SILICON NITRIDE MEMBRANE

(71) Applicant: Applied Materials, Inc., Santa Clara, CA (US)

(72) Inventors: Ryan Scott Smith, Clifton Park, NY (US); Roger Quon, Rhinebeck, NY (US); David Collins, Delmar, NY (US); George Odlum, Red Hook, NY (US); Raghav Sreenivasan, Fremont, CA (US); Joseph R. Johnson, Redwood City, CA (US)

(73) Assignee: APPLIED MATERIALS, INC., Santa Clara, CA (US)

( * ) Notice: Subject to any disclaimer, the term of this patent is extended or adjusted under 35 U.S.C. 154(b) by 461 days.

(21) Appl. No.: 16/933,597

(22) Filed: Jul. 20, 2020

(65) Prior Publication Data
US 2022/0016628 A1    Jan. 20, 2022

(51) Int. Cl.
*B01L 3/00* (2006.01)
*B82B 1/00* (2006.01)
(Continued)

(52) U.S. Cl.
CPC ........ *B01L 3/502753* (2013.01); *B82B 1/005* (2013.01); *B82B 3/008* (2013.01);
(Continued)

(58) Field of Classification Search
None
See application file for complete search history.

(56) References Cited

U.S. PATENT DOCUMENTS 7,402,944 B2   7/2008   Jeong et al.
9,194,860 B2   11/2015  Peng et al.
(Continued)

FOREIGN PATENT DOCUMENTS

CN    104458813 A    3/2015
JP    2007042467 A   2/2007
(Continued)

OTHER PUBLICATIONS

King, Sean et al., "Intrinsic stress effect on fracture toughness of plasma enhanced chemical vapor deposited SiNx: H films", Thin Solid Films, 2010, vol. 518, No. 17, pp. 4898-4907.
(Continued)

*Primary Examiner* — J. Christopher Ball
(74) *Attorney, Agent, or Firm* — PATTERSON + SHERIDAN, LLP

(57) ABSTRACT

Embodiments of the present disclosure provide nanopore devices, such as nanopore sensors and/or other nanofluidic devices. In one or more embodiments, a nanopore device contains a substrate, an optional lower protective oxide layer disposed on the substrate, a membrane disposed on the lower protective oxide layer, and an optional upper protective oxide layer disposed on the membrane. The membrane has a pore and contains silicon nitride. The silicon nitride has a nitrogen to silicon ratio of about 0.98 to about 1.02 and the membrane has an intrinsic stress value of about −1,000 MPa to about 1,000 MPa. The nanopore device also contains a channel extending through at least the substrate, the lower protective oxide layer, the membrane, the upper protective oxide layer, and the upper protective silicon nitride layer.

20 Claims, 5 Drawing Sheets

(51) Int. Cl.
- *B82B 3/00* (2006.01)
- *G01N 27/447* (2006.01)
- *G01N 33/487* (2006.01)
- *G01N 27/40* (2006.01)

(52) U.S. Cl.
CPC ....... *G01N 27/40* (2013.01); *G01N 27/44791* (2013.01); *G01N 33/48721* (2013.01); *B01L 2200/0647* (2013.01); *B01L 2300/0896* (2013.01); *B01L 2300/12* (2013.01)

(56) References Cited

U.S. PATENT DOCUMENTS

| | | | |
|---|---|---|---|
| 9,201,057 B2 | 12/2015 | Peng et al. | |
| 9,515,093 B2 | 12/2016 | Xun et al. | |
| 9,741,557 B1 | 8/2017 | Dellas et al. | |
| 10,032,803 B2 | 7/2018 | Xun et al. | |
| 2005/0159017 A1* | 7/2005 | Kim | C23C 16/45553 438/791 |
| 2005/0269946 A1 | 12/2005 | Jeong et al. | |
| 2006/0111244 A1 | 5/2006 | Gan et al. | |
| 2014/0131202 A1 | 5/2014 | Peng et al. | |
| 2014/0131203 A1 | 5/2014 | Peng et al. | |
| 2015/0200212 A1 | 7/2015 | Xun et al. | |
| 2017/0053940 A1 | 2/2017 | Xun et al. | |
| 2020/0393456 A1 | 12/2020 | Alexandrakis et al. | |

FOREIGN PATENT DOCUMENTS

| | | |
|---|---|---|
| WO | 2017223541 A1 | 12/2017 |
| WO | 2019118495 A1 | 6/2019 |

OTHER PUBLICATIONS

Ma, Hong-Ping et al., "Measurements of microstructural, chemical, optical, and electrical properties of silicon oxygen-nitrogen films prepared by plasma-enhanced atomic layer deposition", Nanomaterials, 2018, vol. 8, No. 12, inner pp. 1-14.

International Search Report and Written Opinion dated Sep. 29, 2021 for Application No. PCT/US2021/036523.

* cited by examiner

NANOFLUIDIC DEVICE WITH SILICON NITRIDE MEMBRANE

BACKGROUND

Field

Embodiments herein relate to flow cells to be used with solid-state nanopore sensors and methods of manufacturing such flow cells.

Description of the Related Art

Solid-state nanopore sensors and other nanofluidic devices have emerged as a low-cost, easily transportable, and rapid processing biopolymer, e.g., DNA or RNA, sequencing technology. Solid-state nanopore sequencing of a biopolymer strand typically incudes translocating a biopolymer strand through one or more nanoscale sized openings (e.g., nanopore) each having a diameter of about 100 nm. In a single pore sensor, a nanopore is disposed through a membrane layer which is positioned in the fluid channel of the device. The biopolymer strand to be sequenced, e.g., a characteristically negatively charged DNA or RNA strand, is introduced into the channel and is then drawn through the nanopore by providing an electric potential across the membrane. As the biopolymer strand travels through the nanopore the different monomer units thereof, e.g., protein bases of a DNA or RNA strand, occlude different percentages of the nanopore thus changing the ionic current flow therethrough. The resulting current signal pattern can be used to determine the sequence of monomer units in the biopolymer strand, such as the sequence of proteins in a DNA or RNA strand.

The nanopore sensors are typically exposed to a variety of chemical environments while in use. The membrane and the nanopore of the nanopore sensor may be exposed to salt solutions, acidic or basic compounds, etchants, oxidizing agents, and/or other compounds or reagents. The membrane can also be exposed to stress. Exposures to such chemicals and/or conditions cause the membrane to crack, spall, oxidize, and/or otherwise degrade. The composition of the membrane changes can be altered due to chemical exposure. For example, the silicon concentration and the nitrogen concentration will be decreased as the oxygen concentration is increased via oxidation of the membrane. In some situations, the membrane is eroded or oxidized around the perimeter of the nanopore such that the pore diameter is increased to a level which inhibits the use of the nanopore sensor.

Accordingly, there is a need for improved nanopore sensors which are more robust in a variety of chemical and/or conditional environments over existing sensors.

SUMMARY

Embodiments of the present disclosure provide nanopore devices, such as nanopore sensors and/or other nanofluidic devices, which may be used for biomolecule sequencing biopolymers (e.g., DNA or RNA) and/or other sensing or monitoring processes. In one or more embodiments, a nanopore device contains a substrate, an optional lower protective oxide layer disposed on the substrate, a membrane disposed on the optional lower protective oxide layer, and an optional upper protective oxide layer disposed on the membrane. The membrane has a pore and contains silicon nitride. In one or more examples, the silicon nitride has a nitrogen to silicon ratio of about 0.98 to about 1.02 and the membrane has an intrinsic stress value of about −1,000 MPa to about 1,000 MPa. The nanopore device also contains a channel extending through at least the substrate, the optional lower protective oxide layer, the membrane, the optional upper protective oxide layer, and the upper protective silicon nitride layer.

In other embodiments, a nanopore device contains a substrate, an optional lower protective oxide layer disposed on the substrate, and a membrane disposed on or above the optional lower protective oxide layer. The membrane has a pore and contains silicon nitride. In some examples, the silicon nitride has a nitrogen to silicon ratio of about 0.95 to about 1.05 and the membrane contains hydrogen at a concentration of about $1\times10^{17}$ atoms/cm$^3$ to less than $1\times10^{20}$ atoms/cm$^3$. The membrane has a thickness of about 0.001 μm to less than 0.1 μm and the pore has a diameter of about 1 nm to less than 100 nm. The nanopore device also includes an optional upper protective oxide layer disposed on or above the membrane and a channel containing the pore and extending through at least the substrate, the lower protective oxide layer, and the upper protective oxide layer.

In some embodiments, a nanopore device contains a substrate, a lower protective silicon nitride layer disposed on a lower surface of the substrate, a lower protective oxide layer disposed on an upper surface of the substrate, and a membrane disposed on the lower protective oxide layer. The membrane has a pore and contains silicon nitride. The silicon nitride has a nitrogen to silicon ratio of about 0.95 to about 1.05 and the membrane contains hydrogen at a concentration of about $1\times10^{17}$ atoms/cm$^3$ to less than $1\times10^{20}$ atoms/cm$^3$. The nanopore device also contains an upper protective oxide layer disposed on the membrane, an upper protective silicon nitride layer disposed on the upper protective oxide layer, and a channel containing the pore and extending through at least the substrate, the lower protective oxide layer, the upper protective oxide layer, and the upper protective silicon nitride layer.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

To facilitate understanding, identical reference numerals have been used, where possible, to designate identical elements that are common to the Figures. It is contemplated that elements and features of one or more embodiments may be beneficially incorporated in other embodiments.

DETAILED DESCRIPTION

Embodiments of the present disclosure provide nanopore devices, such as solid state nanopore sensors and/or other nanofluidic devices, which may be used for biopolymer sequencing and/or other related methods. Generally, the nanopore sensors described and discussed herein are formed by electronics manufacturing techniques which include combinations of multiple processes for deposition, lithography, and etching. The nanopore sensors include a membrane which contains a silicon nitride having properties which enhance the use and longevity of the nanopore sensor.

Figure 1:
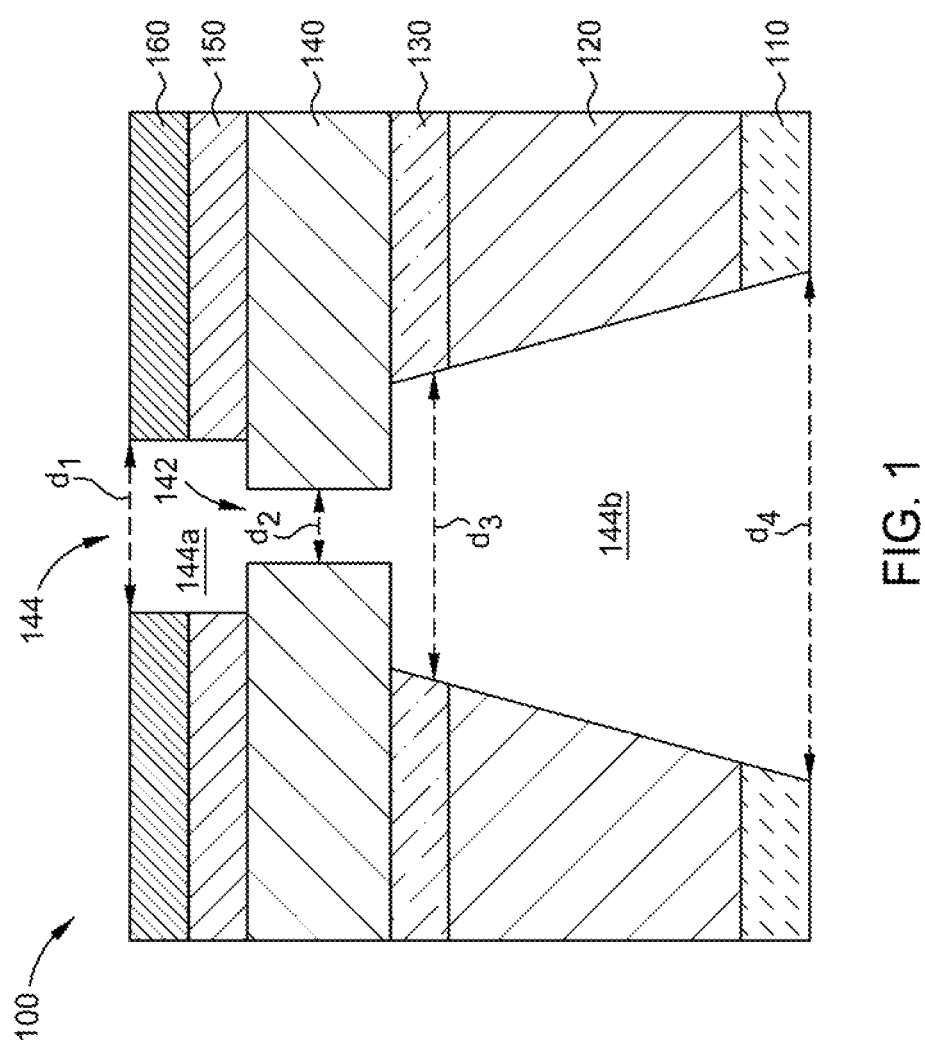
FIG. 1 depicts a schematic cross-sectional view of a nanofluidic device having a membrane containing silicon nitride, according to one or more embodiments described and discussed herein.

FIG. 1 depicts a schematic cross-sectional view of a nanofluidic device 100, according to one or more embodiments described and discussed herein. The nanopore device 100 contains a substrate 120, a lower protective silicon nitride layer 110 disposed on a lower surface of the substrate 120, a lower protective oxide layer 130 disposed on an upper surface of the substrate 120, and a membrane 140 disposed on the lower protective oxide layer 130. The membrane 140 has a pore 142 and contains silicon nitride. The nanopore device 100 also contains an upper protective oxide layer 150 disposed on the membrane 140, and an upper protective silicon nitride layer 160 disposed on the upper protective oxide layer 150.

A channel 144 is formed or otherwise extends through all of the layers of the nanofluidic device 100 including the lower protective silicon nitride layer 110, the substrate 120, the lower protective oxide layer 130, the membrane 140, the upper protective oxide layer 150, and the upper protective silicon nitride layer 160. The channel 144 includes an upper portion 144a, a lower portion 144b, and the pore 142 which separates the upper portion 144a and the lower portion 144b. The upper portion 144a of the channel 144 extends through the upper protective oxide layer 150 and the upper protective silicon nitride layer 160, while the lower portion 144b of the channel 144 extends through the lower protective silicon nitride layer 110, the substrate 120, and the lower protective oxide layer 130. The pore 142 extends through the membrane 140 and is in fluid communication to and disposed between the upper portion 144a and the lower portion 144b.

In one or more examples, the pore 142 is at least partially vertically aligned to the upper portion 144a, the lower portion 144b, and/or both the upper portion 144a and the lower portion 144b. In some examples, the pore 142 is at least substantially coaxial or completely coaxial to the upper portion 144a, the lower portion 144b, and/or both the upper portion 144a and the lower portion 144b. In other examples, the pore 142 is off-centered relative to the upper portion 144a, the lower portion 144b, and/or both the upper portion 144a and the lower portion 144b.

The channel 144 has different distances or diameters along the length of the nanofluidic device 100, as depicted in FIG. 1. The upper portion 144a of the channel 144 has a distance or diameter ($d_1$), the pore 142 has a distance or diameter ($d_2$), and the lower portion 144b of the channel 144 has an increasing diameter from a distance or diameter ($d_3$) in the upper segment to a distance or diameter ($d_4$) in the lower segment. More specifically, the lower portion 144b of the channel 144 has a frustopyramidal or frustum geometry or a frustoconical geometry where the smaller distance or diameter ($d_3$) is measured in the lower protective oxide layer 130 (or at the upper most inner surfaces of the substrate 120 if the lower protective oxide layer 130 is omitted) and the larger distance or diameter ($d_4$) is measured in the lower protective silicon nitride layer 110. In one or more examples, the lower portion 144b of the channel 144 has a rectangular, square, or triangular frustopyramidal or frustum geometry such that each of the upper segment at distance ($d_3$) and the lower segment at distance ($d_4$) is a rectangle (e.g., square), triangle, or other polygonal shape.

The upper portion 144a of the channel 144 has a distance or diameter ($d_1$) of about 1 μm, about 2 μm, about 3 μm, about 5 μm, about 8 μm, about 10 μm, about 20 μm, about 30 μm, about 50 μm, or about 80 μm to about 100 μm, about 120 μm, about 150 μm, about 200 μm, about 250 μm, about 300 μm, about 400 μm, or about 500 μm. For example, the upper portion 144a of the channel 144 has a distance or diameter ($d_1$) of about 1 μm to about 500 μm, about 5 μm to about 500 μm, about 5 μm to about 400 μm, about 5 μm to about 300 μm, about 5 μm to about 200 μm, about 5 μm to about 100 μm, about 5 μm to about 80 μm, about 5 μm to about 50 μm, about 5 μm to about 20 μm, about 10 μm to about 500 μm, about 10 μm to about 400 μm, about 10 μm to about 300 μm, about 10 μm to about 200 μm, about 10 μm to about 100 μm, about 10 μm to about 80 μm, about 10 μm to about 50 μm, about 10 μm to about 20 μm, about 100 μm to about 500 μm, about 100 μm to about 400 μm, about 100 μm to about 300 μm, about 100 μm to about 200 μm, or about 100 μm to about 150 μm.

The pore 142 has a distance or diameter ($d_2$) of about 1 nm, about 2 nm, about 5 nm, about 8 nm, about 10 nm, or about 15 nm to about 18 nm, about 20 nm, about 25 nm, about 30 nm, about 50 nm, about 65 nm, about 80 nm, about 90 nm, about 95 nm, or less than 100 nm. For example, the pore 142 has a distance or diameter ($d_2$) of about 1 nm to less than 100 nm, about 2 nm to less than 100 nm, about 5 nm to less than 100 nm, about 10 nm to less than 100 nm, about 15 nm to less than 100 nm, about 20 nm to less than 100 nm, about 30 nm to less than 100 nm, about 40 nm to less than 100 nm, about 50 nm to less than 100 nm, about 75 nm to less than 100 nm, about 1 nm to about 80 nm, about 2 nm to about 80 nm, about 5 nm to about 80 nm, about 10 nm to about 80 nm, about 15 nm to about 80 nm, about 20 nm to about 80 nm, about 30 nm to about 80 nm, about 40 nm to about 80 nm, about 50 nm to about 80 nm, about 75 nm to about 80 nm, about 1 nm to about 50 nm, about 2 nm to about 50 nm, about 5 nm to about 50 nm, about 10 nm to about 50 nm, about 15 nm to about 50 nm, about 20 nm to about 50 nm, about 30 nm to about 50 nm, or about 40 nm to about 50 nm.

The lower portion 144b of the channel 144 has a smaller distance or diameter ($d_3$) in the upper segment of about 10 μm, about 30 μm, about 50 μm, about 80 μm, or about 100 μm to about 150 μm, about 200 μm, about 300 μm, about 500 μm, about 650 μm, about 800 μm, about 900 μm, or about 1,000 μm. For example, the lower portion 144b of the channel 144 has a smaller distance or diameter ($d_3$) in the upper segment of about 10 μm to about 1,000 μm, about 10 μm to about 900 μm, about 10 μm to about 800 μm, about 10 μm to about 600 μm, about 10 μm to about 500 μm, about 10 μm to about 400 μm, about 10 μm to about 200 μm, about 10 μm to about 100 μm, about 100 μm to about 1,000 μm, about 100 μm to about 900 μm, about 100 μm to about 800

μm, about 100 μm to about 600 μm, about 100 μm to about 500 μm, about 100 μm to about 400 μm, about 100 μm to about 200 μm, about 100 μm to about 150 μm, about 250 μm to about 1,000 μm, about 250 μm to about 900 μm, about 250 μm to about 800 μm, about 250 μm to about 600 μm, about 250 μm to about 500 μm, about 250 μm to about 400 μm, or about 250 μm to about 300 μm.

The lower portion 144b of the channel 144 has a larger distance or diameter ($d_4$) in the lower segment of about 20 μm, about 50 μm, about 80 μm, about 100 μm, or about 150 μm to about 180 μm, about 200 μm, about 300 μm, about 500 μm, about 650 μm, about 800 μm, about 900 μm, about 1,000 μm, about 1,500 μm, about 2,000 μm, about 3,000 μm, or greater. For example, the lower portion 144b of the channel 144 has a larger distance or diameter ($d_4$) in the lower segment of about 20 μm to about 3,000 μm, about 20 μm to about 2,000 μm, about 20 μm to about 1,500 μm, about 20 μm to about 1,000 μm, about 20 μm to about 900 μm, about 20 μm to about 800 μm, about 20 μm to about 600 μm, about 20 μm to about 500 μm, about 20 μm to about 400 μm, about 20 μm to about 200 μm, about 20 μm to about 100 μm, about 100 μm to about 3,000 μm, about 100 μm to about 2,000 μm, about 100 μm to about 1,500 μm, about 100 μm to about 1,000 μm, about 100 μm to about 900 μm, about 100 μm to about 800 μm, about 100 μm to about 600 μm, about 100 μm to about 500 μm, about 100 μm to about 400 μm, about 100 μm to about 200 μm, about 100 μm to about 150 μm, about 250 μm to about 3,000 μm, about 250 μm to about 2,000 μm, about 250 μm to about 1,500 μm, about 250 μm to about 1,000 μm, about 250 μm to about 900 μm, about 250 μm to about 800 μm, about 250 μm to about 600 μm, about 250 μm to about 500 μm, about 250 μm to about 400 μm, or about 250 μm to about 300 μm.

FIGS. 2A-2I depict schematic cross-sectional views of a workpiece 200 during different stages of forming a nanofluidic device, according to one or more embodiments described and discussed herein. The operations used to prepare the nanofluidic device illustrated as the workpiece 200 in FIG. 2I can be used to prepare the nanofluidic device 100 illustrated in FIG. 1.

Figure 2A:
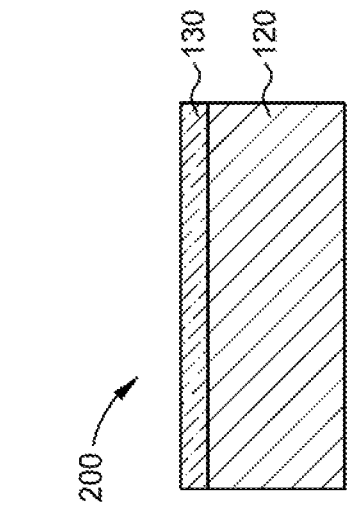
FIGS. 2A-2I depict schematic cross-sectional views of a workpiece during different stages of forming a nanofluidic device, according to one or more embodiments described and discussed herein.

FIG. 2A depicts the workpiece 200 containing the lower protective oxide layer 130 deposited or otherwise formed on the upper surface of the substrate 120. The substrate 120 can be or include any type of substrate useful for forming the nanofluidic device described and discussed herein. Exemplary substrates, wafers, or layers used as the substrate 120 can be or include those commonly used in semiconductor or microelectronic device manufacturing, such as an N-type or P-type doped monocrystalline silicon wafers, or substrates formed undoped monocrystalline silicon, e.g., intrinsic monocrystalline silicon wafers. In some embodiments, the substrate 120 is a doped or undoped silicon substrate or wafer having an epitaxial layer of undoped monocrystalline silicon formed thereon. In other embodiments, the substrate 120 features a layered stack of silicon, an electrically insulating material, such as sapphire or a silicon oxide, and silicon, commonly known as a silicon-on-insulator (SOI) substrate or an SOI wafer. When used as the substrate 120, undoped silicon substrates, undoped silicon epitaxial layers, and SOI substrates beneficially reduce undesirable parasitic capacitance in a nanopore sensor formed therefrom when compared to a sensor formed of a doped silicon substrate.

The substrate 120 has a thickness of about 200 μm, about 250 μm, about 300 μm, about 500 μm, about 750 μm, about 1,000 μm, or about 1,500 μm to about 2,000 μm, about 3,000 μm, about 5,000 μm, about 7,000 μm, about 10,000 μm, about 12,000 μm, about 15,000 μm, about 18,000 μm, or about 20,000 μm. For example, the substrate 120 can have a thickness of about 200 μm to about 20,000 μm, about 500 μm to about 20,000 μm, about 1,000 μm to about 20,000 μm, about 3,000 μm to about 20,000 μm, about 5,000 μm to about 20,000 μm, about 10,000 μm to about 20,000 μm, about 200 μm to about 10,000 μm, about 500 μm to about 10,000 μm, about 1,000 μm to about 10,000 μm, about 3,000 μm to about 10,000 μm, about 5,000 μm to about 10,000 μm, about 8,000 μm to about 10,000 μm, about 200 μm to about 2,000 μm, about 500 μm to about 2,000 μm, about 1,000 μm to about 2,000 μm, or about 1,500 μm to about 2,000 μm.

The lower protective oxide layer 130 contains one or more oxides, such as silicon oxides, which includes silicon dioxide, silane oxide, silica, silicates, dopants thereof, or any combination thereof. The lower protective oxide layer 130 can be deposited by one or more vapor deposition processes and/or one or more thermal growth processes. Exemplary deposition or growth processes can be or include chemical vapor deposition (CVD), plasma-enhanced CVD (PE-CVD), pulsed-CVD, atomic layer deposition (ALD), plasma-enhanced ALD (PE-ALD), physical vapor deposition (PVD), sputtering techniques, thermally grown oxidation processes, or any combination thereof.

The lower protective oxide layer 130 has a thickness of about 2 nm, about 5 nm, about 10 nm, about 15 nm, about 18 nm, about 20 nm, about 25 nm, about 30 nm or about 50 nm to about 65 nm, about 80 nm, about 90 nm, about 100 nm, about 150 nm, about 200 nm, about 250 nm, or about 300 nm. For example, the lower protective oxide layer 130 has a thickness of about 2 nm to about 300 nm, about 5 nm to about 300 nm, about 10 nm to about 300 nm, about 20 nm to about 300 nm, about 30 nm to about 300 nm, about 40 nm to about 300 nm, about 50 nm to about 300 nm, about 75 nm to about 300 nm, about 100 nm to about 300 nm, about 150 nm to about 300 nm, about 200 nm to about 300 nm, about 250 nm to about 300 nm, about 2 nm to about 200 nm, about 5 nm to about 200 nm, about 10 nm to about 200 nm, about 20 nm to about 200 nm, about 30 nm to about 200 nm, about 40 nm to about 200 nm, about 50 nm to about 200 nm, about 75 nm to about 200 nm, about 100 nm to about 200 nm, about 150 nm to about 200 nm, about 2 nm to about 100 nm, about 5 nm to about 100 nm, about 10 nm to about 100 nm, about 20 nm to about 100 nm, about 30 nm to about 100 nm, about 40 nm to about 100 nm, about 50 nm to about 100 nm, about 75 nm to about 100 nm, about 20 nm to about 80 nm, about 30 nm to about 80 nm, about 40 nm to about 80 nm, about 50 nm to about 80 nm, about 20 nm to about 100 nm, about 20 nm to about 90 nm, about 20 nm to about 80 nm, or about 20 nm to about 40 nm.

Figure 2B:
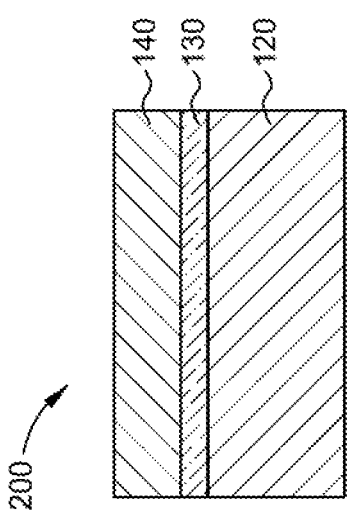

FIG. 2B depicts the workpiece 200 containing the membrane 140 deposited or otherwise formed on the lower protective oxide layer 130. The membrane 140 contains silicon nitride having a nitrogen to silicon ratio of about 1. The membrane 140 can be deposited by one or more vapor deposition processes. In one or more examples, the membrane 140 can be deposited by a PVD process, as further described and discussed below. In other examples, the membrane 140 can be deposited by CVD, PE-CVD, pulsed-CVD, low pressure CVD (LP-CVD), ALD, PE-ALD, or any combination thereof.

In one or more embodiments, the membrane 140 containing silicon nitride is deposited by a PVD process. The PVD process can use a pulsed DC power supply set with an output of 0 kW or about 0.1 kW to about 10 kW coupled to a silicon sputter target. The substrate or workpiece is electrostatically chucked and heated to a temperature of about 200° C. to about 400° C. A mixture of argon and nitrogen ($N_2$) is introduced into the processing region of the chamber with dedicated mass flow controllers, enabling independent control of the flow rates for the argon and nitrogen gases. The gas pressure is controlled by varying the total flow while using a cryogenic pump to maintain pressures in the milli-Torr (mTorr) range, such as about 1 mTorr to about 100 mTorr. The stoichiometry, texture, deposition rate, and uniformity of the deposited silicon nitride film can be varied by changing the target power, the total gas pressure, the $Ar/N_2$ flow ratio, and the wafer temperature. In some examples, the $Ar/N_2$ flow ratio can be from about 1:1 to about 4:1, which can be adjusted for controlling the Si:N ratio in the deposited silicon nitride of the membrane 140. In one or more examples, the PVD process uses a pulsed DC power (e.g., target power) of about 1 kW to about 5 kW, a process chamber pressure of about 1 mTorr to about 10 mTorr, and the substrate or workpiece heated to about 200° C. to about 400° C.

After the membrane 140 is deposited on the lower protective oxide layer 130, the workpiece 200 containing the membrane 140 is treated with a thermal anneal. The workpiece 200 is heated to a temperature of about 800° C., about 900° C., or about 950° C. to about 1,000° C., about 1050° C., about 1,100° C., or about 1,200° C. for about 20 minutes, about 30 minutes, about 45 minutes, or about 60 minutes to about 75 minutes, about 90 minutes, about 120 minutes, or about 150 minutes. The workpiece 200 containing the membrane 140 is heated in a processing chamber or anneal chamber containing an environment of process gas, such as nitrogen ($N_2$), argon, helium, or any combination thereof, and can be maintained at sub-atmospheric pressure, atmospheric pressure, or over-pressure. In one or more examples, the workpiece 200 containing the membrane 140 is heated at about 1,000° C. for about 60 minutes in an environment of nitrogen gas at atmospheric pressure (about 760 Torr).

In one or more embodiments, the silicon nitride contained in the membrane 140 has a nitrogen to silicon ratio of about 0.95, about 0.96, about 0.97, about 0.98, about 0.99, or about 1.00 to about 1.01, about 1.02, about 1.03, about 1.04, or about 1.05. For example, the silicon nitride contained in the membrane 140 has a nitrogen to silicon ratio of about 0.95 to about 1.05, about 0.95 to about 1.04, about 0.95 to about 1.03, about 0.95 to about 1.02, about 0.95 to about 1.01, about 0.95 to about 1.00, about 0.95 to about 0.99, about 0.95 to about 0.98, about 0.95 to about 0.97, about 0.98 to about 1.05, about 0.98 to about 1.04, about 0.98 to about 1.03, about 0.98 to about 1.02, about 0.98 to about 1.01, about 0.98 to about 1.00, about 0.98 to about 0.99, about 0.99 to about 1.05, about 0.99 to about 1.04, about 0.99 to about 1.03, about 0.99 to about 1.02, about 0.99 to about 1.01, or about 0.99 to about 1.00.

The membrane 140 can have a relatively high concentration of elemental silicon and relative low concentrations of hydrogen, oxygen, and/or other elements. In some embodiments, the membrane 140 can substantially or completely lack elemental silicon. The membrane 140 can have elemental silicon at a concentration of about 0 atomic percent (at %), about 0.01 at %, about 0.1 at %, about 0.5 at %, about 1 at %, about 2 at %, about 3 at %, about 4 at %, or about 5 at % to about 6 at %, about 7 at %, about 8 at %, about 9 at %, about 10 at %, or more. For example, the membrane 140 has elemental silicon at a concentration of about 0.01 at % to about 10 at %, about 0.1 at % to about 10 at %, about 0.5 at % to about 10 at %, about 1 at % to about 10 at %, about 2 at % to about 10 at %, about 3 at % to about 10 at %, about 5 at % to about 10 at %, about 6 at % to about 10 at %, about 7 at % to about 10 at %, about 8 at % to about 10 at %, about 0.1 at % to about 7 at %, about 0.5 at % to about 7 at %, about 1 at % to about 7 at %, about 2 at % to about 7 at %, about 3 at % to about 7 at %, about 5 at % to about 7 at %, about 6 at % to about 7 at %, about 0.1 at % to about 5 at %, about 0.5 at % to about 5 at %, about 1 at % to about 5 at %, about 2 at % to about 5 at %, about 3 at % to about 5 at %, or about 4 at % to about 5 at %.

The membrane 140 has hydrogen at a concentration of less than $1\times10^{20}$ atoms/$cm^3$. For example, the membrane 140 has hydrogen at a concentration of about $1\times10^{17}$ atoms/$cm^3$ to less than $1\times10^{20}$ atoms/$cm^3$, about $1\times10^{18}$ atoms/$cm^3$ to less than $1\times10^{20}$ atoms/$cm^3$, or about $1\times10^{19}$ atoms/$cm^3$ to less than $1\times10^{20}$ atoms/$cm^3$. The membrane 140 has oxygen at a concentration of less than $2\times10^{20}$ atoms/$cm^3$. For example, the membrane 140 has oxygen at a concentration of about $1\times10^{18}$ atoms/$cm^3$ to less than $2\times10^{20}$ atoms/$cm^3$, about $1\times10^{19}$ atoms/$cm^3$ to less than $2\times10^{20}$ atoms/$cm^3$, about $1\times10^{18}$ atoms/$cm^3$ to about $1\times10^{20}$ atoms/$cm^3$, or about $1\times10^{19}$ atoms/$cm^3$ to about $1\times10^{20}$ atoms/$cm^3$.

The membrane 140 has a thickness of about 0.001 μm, about 0.005 μm, about 0.007 μm, or about 0.01 μm to about 0.02 μm, about 0.025 μm, about 0.035 μm, about 0.05 μm, about 0.065 μm, about 0.08 μm, about 0.09 μm, or less than 0.1 μm. The membrane 140 has a thickness of about 0.001 μm to less than 0.1 μm, about 0.005 μm to less than 0.1 μm, about 0.007 μm to less than 0.1 μm, about 0.01 μm to less than 0.1 μm, about 0.02 μm to less than 0.1 μm, about 0.05 μm to less than 0.1 μm, about 0.065 μm to less than 0.1 μm, about 0.08 μm to less than 0.1 μm, about 0.001 μm to about 0.09 μm, about 0.005 μm to about 0.09 μm, about 0.007 μm to about 0.09 μm, about 0.01 μm to about 0.09 μm, about 0.02 μm to about 0.09 μm, about 0.05 μm to about 0.09 μm, about 0.065 μm to about 0.09 μm, about 0.007 μm to about 0.09 μm, about 0.08 μm to about 0.09 μm, about 0.001 μm to about 0.065 μm, about 0.005 μm to about 0.065 μm, about 0.007 μm to about 0.065 μm, about 0.01 μm to about 0.065 μm, about 0.02 μm to about 0.065 μm, or about 0.05 μm to about 0.065 μm.

The membrane 140 has an intrinsic stress value of about −1,000 MPa, about −800 MPa, about −700 MPa, −500 MPa, about −300 MPa, or about −100 MPa to about 100 MPa, about 300 MPa, about 500 MPa, about 700 MPa, about 800 MPa, or about 1,000 MPa. For example, the membrane 140 has an intrinsic stress value of about −1,000 MPa to about 1,000 MPa, about −800 MPa to about 800 MPa, about −500 MPa to about 500 MPa, or about −300 MPa to about 300 MPa.

The membrane 140 has a refractive index of about 2, about 2.1, about 2.15, about 2.2, about 2.23, or about 2.25 to about 2.27, about 2.3, about 2.32, about 2.35, about 2.4, about 2.45, or about 2.5. The membrane 140 has a refractive index of about 2 to about 2.5, about 2.1 to about 2.5, about 2.15 to about 2.5, about 2.2 to about 2.5, about 2.23 to about 2.5, about 2.25 to about 2.5, about 2.3 to about 2.5, about 2 to about 2.4, about 2.1 to about 2.4, about 2.15 to about 2.4, about 2.2 to about 2.4, about 2.23 to about 2.4, about 2.25 to about 2.4, about 2.3 to about 2.4, about 2 to about 2.3, about 2.1 to about 2.3, about 2.15 to about 2.3, about 2.2 to about 2.3, about 2.23 to about 2.3, about 2.25 to about 2.3, or about 2.23 to about 2.27.

Figure 2C:
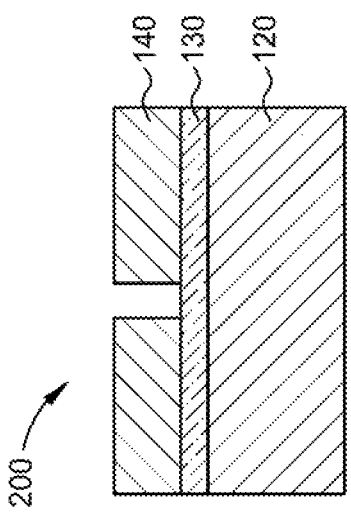

FIG. 2C depicts the workpiece 200 containing a well or void formed in the membrane 140 by a front-side lithography-etch process. The formation of this well or void in the membrane 140 is pore patterning. During subsequent fabrication of the nanofluidic device from the workpiece 200, this well or void is transformed into the pore 142, as depicted in FIG. 2I. The membrane 140 is exposed to a lithography process followed by an etching process to produce the well or void. The well or void can have a straight-walled geometry while extending through the membrane 140 and to the lower protective oxide layer 130.

Figure 2D:
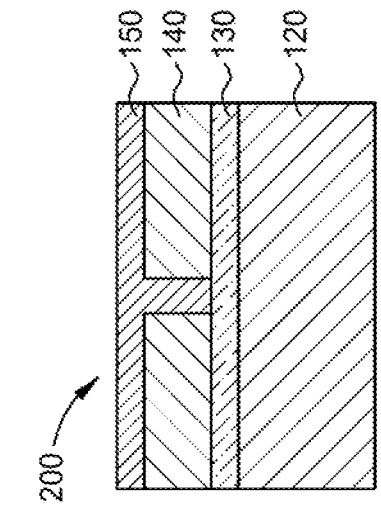

FIG. 2D depicts the workpiece 200 containing the upper protective oxide layer 150 deposited or otherwise formed on in the membrane 140 and within the well or void formed in the membrane 140 (e.g., the pore 142). The well or void formed in the membrane 140 can be substantially or completely filled with the upper protective oxide layer 150. The upper protective oxide layer 150 contains one or more oxides, such as silicon oxides, which includes silicon dioxide, silane oxide, silica, silicates, dopants thereof, or any combination thereof. The upper protective oxide layer 150 can be deposited by one or more vapor deposition processes and/or one or more thermal growth processes. Exemplary deposition or growth processes can be or include CVD, PE-CVD, pulsed-CVD, ALD, PE-ALD, PVD, sputtering techniques, thermally grown oxidation processes, or any combination thereof.

The upper protective oxide layer 150 has a thickness of about 0.5 µm, about 1 µm, about 2 µm, about 3 µm, about 5 µm, about 10 µm, about 15 µm, about 18 µm, about 20 µm, about 25 µm, about 30 µm or about 50 µm to about 65 µm, about 80 µm, about 90 µm, about 100 µm, about 150 µm, about 200 µm, about 250 µm, or about 300 µm. For example, the upper protective oxide layer 150 has a thickness of about 0.5 µm to about 300 µm, about 2 µm to about 300 µm, about 5 µm to about 300 µm, about 10 µm to about 300 µm, about 20 µm to about 300 µm, about 30 µm to about 300 µm, about 40 µm to about 300 µm, about 50 µm to about 300 µm, about 75 µm to about 300 µm, about 100 µm to about 300 µm, about 150 µm to about 300 µm, about 200 µm to about 300 µm, about 250 µm to about 300 µm, about 2 µm to about 200 µm, about 5 µm to about 200 µm, about 10 µm to about 200 µm, about 20 µm to about 200 µm, about 30 µm to about 200 µm, about 40 µm to about 200 µm, about 50 µm to about 200 µm, about 75 µm to about 200 µm, about 100 µm to about 200 µm, about 150 µm to about 200 µm, about 2 µm to about 100 µm, about 5 µm to about 100 µm, about 10 µm to about 100 µm, about 20 µm to about 100 µm, about 30 µm to about 100 µm, about 40 µm to about 100 µm, about 50 µm to about 100 µm, about 75 µm to about 100 µm, about 20 µm to about 80 µm, about 30 µm to about 80 µm, about 40 µm to about 80 µm, about 50 µm to about 80 µm, about 20 µm to about 100 µm, about 20 µm to about 90 µm, about 20 µm to about 80 µm, or about 20 µm to about 40 µm.

Figure 2E:
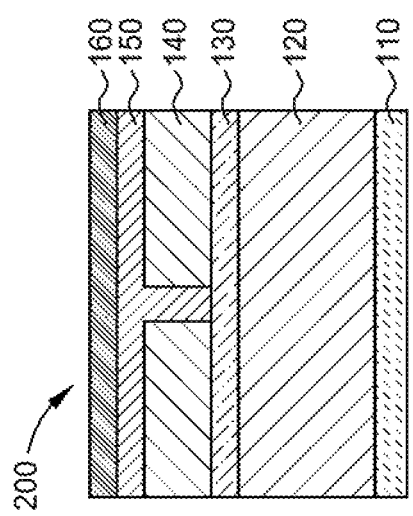

FIG. 2E depicts the workpiece 200 containing the lower protective silicon nitride layer 110 and the upper protective silicon nitride layer 160. The lower protective silicon nitride layer 110 is deposited or otherwise formed on in the lower surface of the substrate 120. The upper protective silicon nitride layer 160 is deposited or otherwise formed on the upper protective oxide layer 150. In one or more examples, the lower protective silicon nitride layer 110 and the upper protective silicon nitride layer 160 are deposited or formed simultaneously in a single deposition process. In other examples, the lower protective silicon nitride layer 110 and the upper protective silicon nitride layer 160 are independently deposited or formed in separate deposition processes.

The lower protective silicon nitride layer 110 and the upper protective silicon nitride layer 160 can independently be deposited by one or more vapor deposition processes. Exemplary vapor deposition processes can be or include LP-CVD, CVD, PE-CVD, pulsed-CVD, ALD, PE-ALD, PVD, sputtering techniques, or any combination thereof. Each of the lower protective silicon nitride layer 110 and the upper protective silicon nitride layer 160 independently contains silicon nitride having a chemical formula of $Si_3N_4$ or $SiN_x$, where x is from about 1 to about 1.33. In one or more examples, the lower protective silicon nitride layer 110 and the upper protective silicon nitride layer 160 contain silicon nitride deposited simultaneously by a LP-CVD process or a PE-CVD process.

Figure 2F:
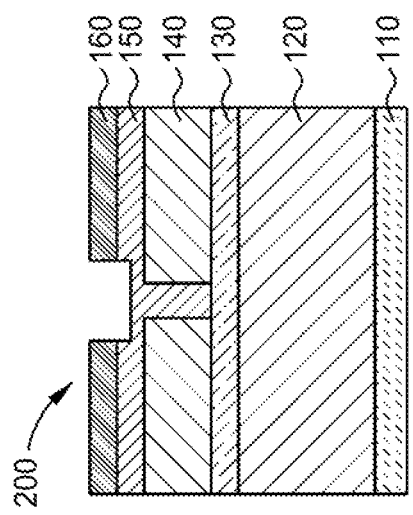
Figure 2I:
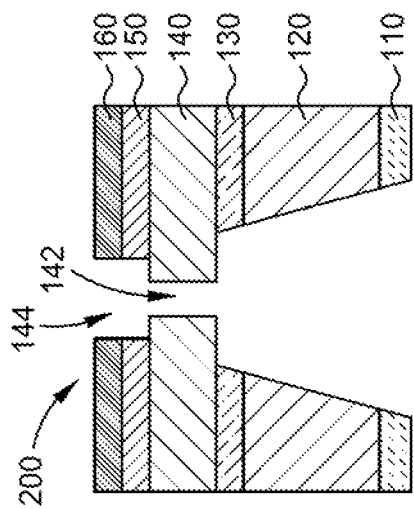

FIG. 2F depicts the workpiece 200 containing a well or void formed in the upper protective oxide layer 150 and the upper protective silicon nitride layer 160 by a front-side lithography-etch process. The well or void is formed completely through the upper protective silicon nitride layer 160 and at least partially through, such as about half way through, the upper protective oxide layer 150 directly above the location future location of the pore 142. The formation of this well or void in the upper protective oxide layer 150 and the upper protective silicon nitride layer 160 is well patterning. During subsequent fabrication of the nanofluidic device from the workpiece 200, this well or void is transformed into the upper portion 144a of the channel 144, as depicted in FIG. 1. The upper protective oxide layer 150 and the upper protective silicon nitride layer 160 are exposed to at least one lithography process followed by an etching process to produce the well or void. The well or void can have a straight-walled geometry while extending through the upper protective oxide layer 150 and the upper protective silicon nitride layer 160.

Figure 2H:
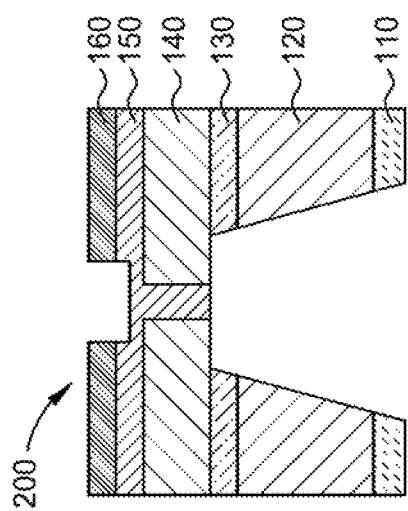
Figure 2G:
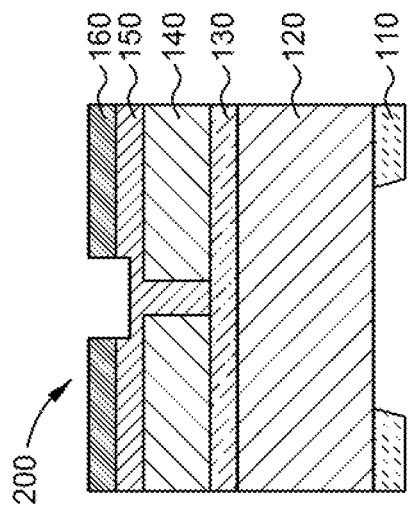

FIG. 2G depicts the workpiece 200 containing a well or void formed in the lower protective silicon nitride layer 110 by a back-side lithography-etch process. The lower protective silicon nitride layer 110 is exposed to a lithography process followed by an etching process to produce the well or void. The well or void extends through the lower protective silicon nitride layer 110 and to the substrate 120.

FIG. 2H depicts the workpiece 200 containing the well or void formed in the lower protective silicon nitride layer 110 further extended through the substrate 120 and lower protective oxide layer 130 by one or more additional back-side lithography-etch processes or wet-etch processes. During subsequent fabrication of the nanofluidic device from the workpiece 200, this well or void is transformed into the lower portion 144b of the channel 144, as depicted in FIG. 1. The substrate 120 and lower protective oxide layer 130 are exposed to at least one lithography process followed by an etching process to produce the well or void. The well or void extends through the substrate 120 and lower protective oxide layer 130 to the membrane 140.

FIG. 2I depicts the workpiece 200 subsequent to fabrication of the nanofluidic device. The well or void shown formed in the upper protective oxide layer 150 depicted in FIG. 2F is further extended by one or more front-side lithography-etch processes or wet-etch processes to form the remainder of the upper portion 144a of the channel 144 and the pore 142. The upper protective oxide layer 150 is exposed to at least one wet-etch process followed by an etching process to produce the channel 144 containing the pore 142. In one or more examples, the wet-etch process includes exposing the workpiece 200 to an etching solution containing about 20 wt % to about 40 wt % or about 25 wt % to about 35 wt % of potassium hydroxide at a temperature of about 60° C. to about 100° C. or about 70° C. to about 90° C. to remove material, such as silicon and/or oxide, at an etch rate of about 50 µm/hour to about 80 µm/hour or about 60 µm/hour to about 70 µm/hour.

Figure 3:
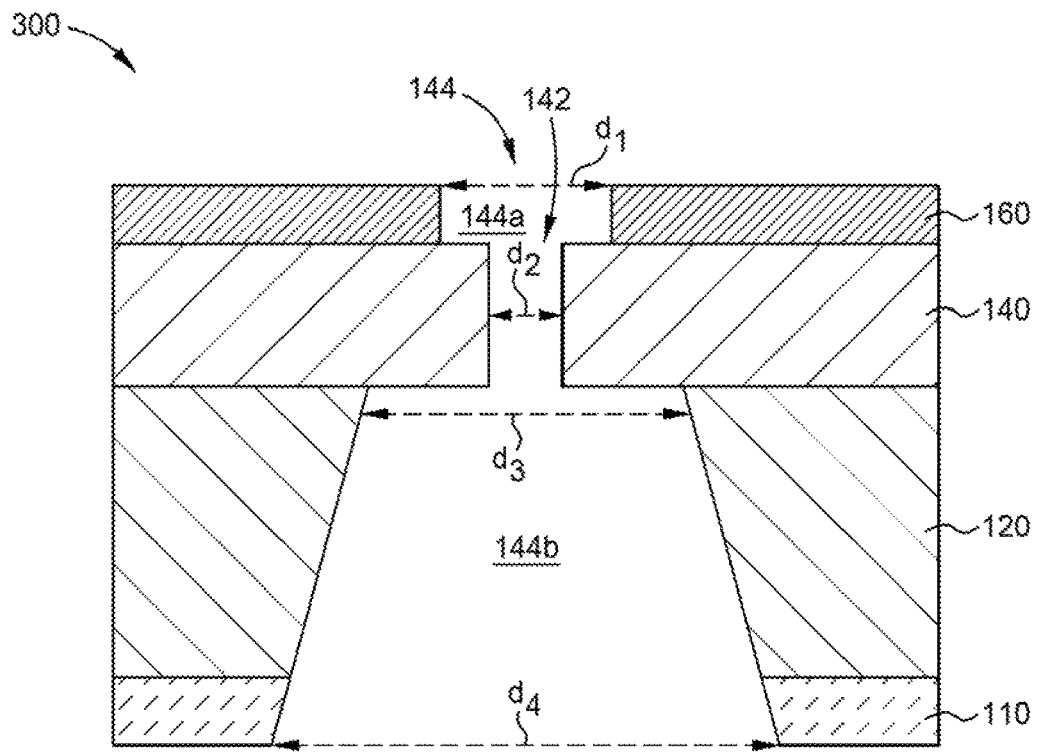
FIG. 3 depicts a schematic cross-sectional view of another nanofluidic device having a membrane containing silicon nitride, according to one or more embodiments described and discussed herein.

FIG. 3 depicts a schematic cross-sectional view of another nanofluidic device 300, according to one or more embodiments described and discussed herein. The nanofluidic device 300 has all of the same layers and features as the nanofluidic device 100, but lacks the lower protective oxide layer 130 and the upper protective oxide layer 150. The nanopore device 300 contains the lower protective silicon nitride layer 110 disposed on a lower surface of the substrate 120, the membrane 140 disposed on the upper surface of the substrate 120, and the upper protective silicon nitride layer 160 disposed on the membrane 140. In some embodiments, the lower protective silicon nitride layer 110 and/or the upper protective silicon nitride layer 160 can independently be omitted from the nanofluidic device 300.

The channel 144 is formed or otherwise extends through all of the layers of the nanofluidic device 300 including the optional lower protective silicon nitride layer 110, the substrate 120, the membrane 140, and the optional upper protective silicon nitride layer 160. The pore 142 separates the upper portion 144a and the lower portion 144b of the channel 144. The upper portion 144a of the channel 144 extends through the upper protective silicon nitride layer 160, while the lower portion 144b of the channel 144 extends through the lower protective silicon nitride layer 110 and the substrate 120. The smaller distance or diameter ($d_3$) within the lower portion 144b is measured in the upper most inner surfaces of the substrate 120.

Figure 4:
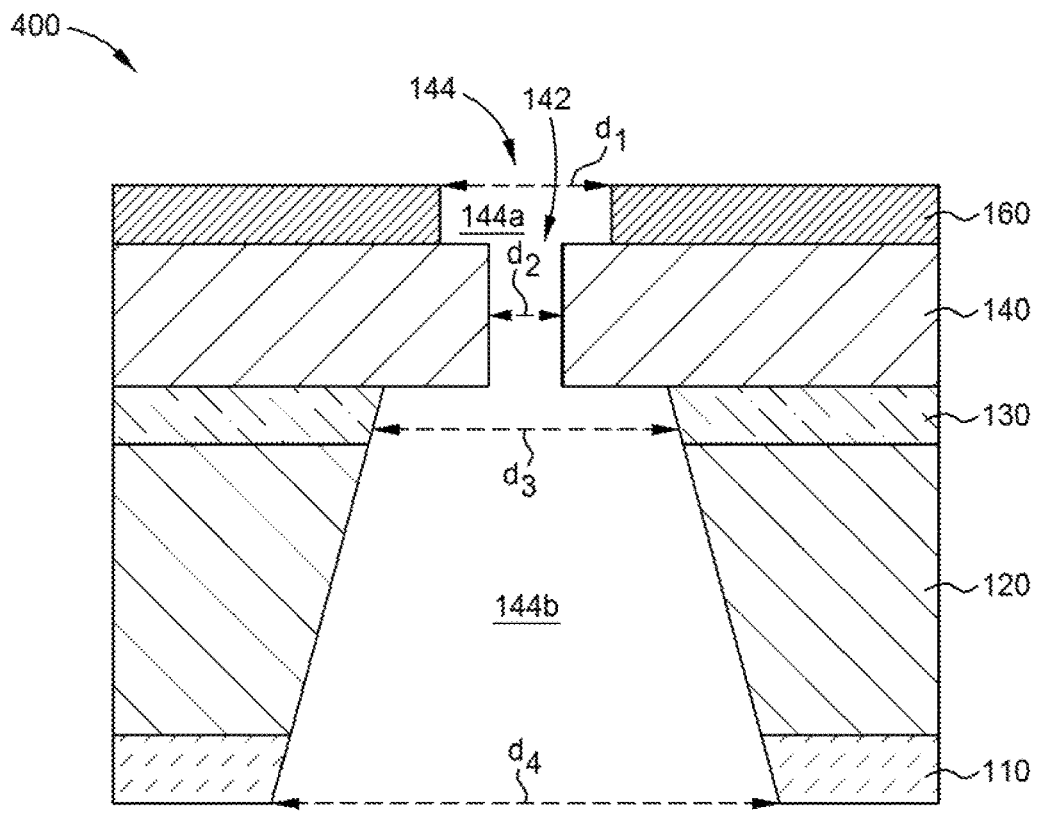
FIG. 4 depicts a schematic cross-sectional view of another nanofluidic device having a membrane containing silicon nitride, according to one or more embodiments described and discussed herein.

FIG. 4 depicts a schematic cross-sectional view of another nanofluidic device 400, according to one or more embodiments described and discussed herein. The nanofluidic device 400 has all of the same layers and features as the nanofluidic device 100, but lacks the upper protective oxide layer 150. The nanopore device 400 contains the lower protective silicon nitride layer 110 disposed on a lower surface of the substrate 120, the lower protective oxide layer 130 disposed on the upper surface of the substrate 120, the membrane 140 disposed on the lower protective oxide layer 130, and the upper protective silicon nitride layer 160 disposed on the membrane 140. In some embodiments, the lower protective silicon nitride layer 110 and/or the upper protective silicon nitride layer 160 can independently be omitted from the nanofluidic device 400.

The channel 144 is formed or otherwise extends through all of the layers of the nanofluidic device 400 including the optional lower protective silicon nitride layer 110, the substrate 120, the lower protective oxide layer 130, the membrane 140, and the optional upper protective silicon nitride layer 160. The pore 142 separates the upper portion 144a and the lower portion 144b of the channel 144. The upper portion 144a of the channel 144 extends through the upper protective silicon nitride layer 160, while the lower portion 144b of the channel 144 extends through the lower protective silicon nitride layer 110, the substrate 120, and lower protective oxide layer 130. The smaller distance or diameter ($d_3$) within the lower portion 144b is measured in the upper most inner surfaces of the lower protective oxide layer 130.

Figure 5:
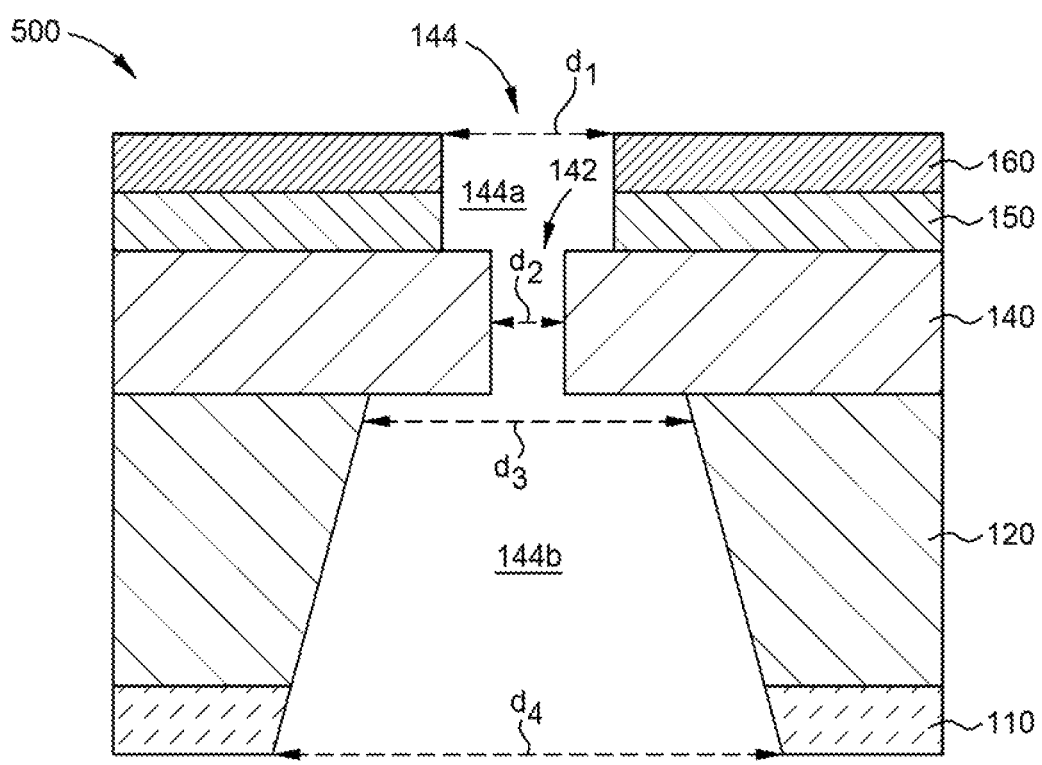
FIG. 5 depicts a schematic cross-sectional view of another nanofluidic device having a membrane containing silicon nitride, according to one or more embodiments described and discussed herein.

FIG. 5 depicts a schematic cross-sectional view of another nanofluidic device 500 having a membrane containing silicon nitride, according to one or more embodiments described and discussed herein. The nanofluidic device 500 has all of the same layers and features as the nanofluidic device 100, but lacks the lower protective oxide layer 130. The nanopore device 500 contains the lower protective silicon nitride layer 110 disposed on a lower surface of the substrate 120, the membrane 140 disposed on the upper surface of the substrate 120, the upper protective oxide layer 150 disposed on the membrane 140, and the upper protective silicon nitride layer 160 disposed on the membrane 140. In some embodiments, the lower protective silicon nitride layer 110 and/or the upper protective silicon nitride layer 160 can independently be omitted from the nanofluidic device 500.

The channel 144 is formed or otherwise extends through all of the layers of the nanofluidic device 500 including the optional lower protective silicon nitride layer 110, the substrate 120, the membrane 140, the upper protective oxide layer 150, and the optional upper protective silicon nitride layer 160. The pore 142 separates the upper portion 144a and the lower portion 144b of the channel 144. The upper portion 144a of the channel 144 extends through the upper protective oxide layer 150 and the upper protective silicon nitride layer 160, while the lower portion 144b of the channel 144 extends through the lower protective silicon nitride layer 110 and the substrate 120. The smaller distance or diameter ($d_3$) within the lower portion 144b is measured in the upper most inner surfaces of the substrate 120.

Beneficially, the embodiments of the present disclosure provide nanopore devices, such as solid state nanopore sensors and/or other nanofluidic devices, which may be used for biopolymer sequencing and/or other related methods. These improved nanopore devices/sensors are more robust in a variety of chemical and/or conditional environments over existing sensors/devices. These nanopore devices/sensors include a membrane which contains a silicon nitride having properties which enhance the use and longevity of the nanopore sensor. The silicon nitride of the membrane has a nitrogen to silicon ratio of about 0.95 to about 1.05, such as about 0.98 to about 1.02, about 0.99 to about 1.01, or about 1.00. The silicon nitride of the membrane contains about 0.1 at % to about 10 at % or about 3 at % to about 7 at % of elemental silicon while having hydrogen at a concentration of less than $1\times10^{20}$ atoms/cm$^3$. Also, the membrane has an intrinsic stress value of about −500 MPa to about 500 MPa and a refractive index of about 2.1 to about 2.5.

While the foregoing is directed to embodiments of the disclosure, other and further embodiments may be devised without departing from the basic scope thereof, and the scope thereof is determined by the claims that follow. All documents described herein are incorporated by reference herein, including any priority documents and/or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby. Likewise, the term "comprising" is considered synonymous with the term "including" for purposes of United States law. Likewise, whenever a composition, an element, or a group of elements is preceded with the transitional phrase "comprising", it is understood that the same composition or group of elements with transitional phrases "consisting essentially of", "consisting of", "selected from the group of consisting of", or "is" preceding the recitation of the composition, element, or elements and vice versa, are contemplated.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below.

The invention claimed is:

1. A nanopore device, comprising:
   a substrate;
   a membrane disposed above the substrate, wherein:
      the membrane comprises silicon nitride and contains a pore;
      the silicon nitride has a nitrogen to silicon ratio of about 0.98 to about 1.02;
      the membrane comprises about 0.1 atomic percent (at %) to about 10 at % of elemental silicon;
      the membrane has a refractive index of about 2.1 to about 2.5; and
      the membrane has an intrinsic stress value of about −1,000 MPa to about 1,000 MPa; and
   a channel containing the pore and extending through at least the substrate.

2. The nanopore device of claim 1, wherein the membrane has an intrinsic stress value of about −500 MPa to about 500 MPa.

3. The nanopore device of claim 1, wherein the membrane has a refractive index of about 2.15 to about 2.45.

4. The nanopore device of claim 1, wherein the membrane comprises hydrogen at a concentration of about $1 \times 10^{17}$ atoms/cm$^3$ to less than $1 \times 10^{20}$ atoms/cm$^3$.

5. The nanopore device of claim 1, wherein the membrane comprises oxygen at a concentration of about $1 \times 10^{18}$ atoms/cm$^3$ to less than $2 \times 10^{20}$ atoms/cm$^3$.

6. The nanopore device of claim 1, further comprising a lower protective oxide layer disposed between and in contact with the substrate and the membrane.

7. The nanopore device of claim 6, further comprising an upper protective oxide layer disposed on the membrane, wherein the membrane is disposed between and in contact with the upper and lower protective oxide layers.

8. The nanopore device of claim 1, wherein the membrane has a thickness of about 0.001 μm to less than 0.1 μm.

9. The nanopore device of claim 1, wherein the pore has a diameter of about 1 nm to less than 100 nm.

10. The nanopore device of claim 1, wherein the membrane comprises about 1 at % to about 8 at % of elemental silicon.

11. The nanopore device of claim 1, wherein the channel comprises an upper portion and a lower portion which are separated by the pore, and wherein the core is at least substantially coaxial with the upper portion, the lower portion, or both.

12. A nanopore device, comprising:
   a substrate;
   a lower protective oxide layer disposed on the substrate;
   a membrane disposed on the lower protective oxide layer, wherein the membrane comprises silicon nitride and contains a pore, and wherein:
      the silicon nitride has a nitrogen to silicon ratio of about 0.95 to about 1.05;
      the membrane comprises hydrogen at a concentration of about $1 \times 10^{17}$ atoms/cm$^3$ to less than $1 \times 10^{20}$ atoms/cm$^3$;
      the membrane has a thickness of about 0.001 μm to less than 0.1 μm; and
      the pore has a diameter of about 1 nm to less than 100 nm; and
   a channel containing the pore and extending through at least the substrate and the lower protective oxide layer.

13. The nanopore device of claim 12, wherein the membrane has an intrinsic stress value of about −500 MPa to about 500 MPa.

14. The nanopore device of claim 12, wherein the membrane has a refractive index of about 2.1 to about 2.5.

15. The nanopore device of claim 12, wherein the membrane comprises oxygen at a concentration of about $1 \times 10^{18}$ atoms/cm$^3$ to less than $2 \times 10^{20}$ atoms/cm$^3$.

16. The nanopore device of claim 12, wherein the silicon nitride has a nitrogen to silicon ratio of about 0.98 to about 1.02.

17. The nanopore device of claim 12, wherein the membrane has a thickness of about 0.001 μm to less than 0.1 μm.

18. The nanopore device of claim 12, wherein the pore has a diameter of about 1 nm to less than 100 nm.

19. The nanopore device of claim 12, wherein the membrane comprises about 0.1 atomic percent (at %) to about 10 at % of elemental silicon.

20. A nanopore device, comprising:
   a substrate;
   a lower protective silicon nitride layer disposed on a lower surface of the substrate;
   a lower protective oxide layer disposed on an upper surface of the substrate;
   a membrane disposed on the lower protective oxide layer, wherein:
      the membrane comprises silicon nitride and contains a pore;
      the silicon nitride has a nitrogen to silicon ratio of about 0.95 to about 1.05; and
      the membrane comprises hydrogen at a concentration of about $1 \times 10^{17}$ atoms/cm$^3$ to less than $1 \times 10^{20}$ atoms/cm$^3$;
   an upper protective oxide layer disposed on the membrane;
   an upper protective silicon nitride layer disposed on the upper protective oxide layer; and
   a channel containing the pore and extending through at least the substrate, the lower protective oxide layer, the upper protective oxide layer, and the upper protective silicon nitride layer.

* * * * *